United States Patent [19]

Veltri et al.

[11] Patent Number: 5,098,933
[45] Date of Patent: Mar. 24, 1992

[54] PHARMACEUTICALLY USEFUL MICHAEL ADDITION PRODUCTS OF UNSATURATED ALDEHYDES AND KETONES AND ASCORBIC ACID

[75] Inventors: Robert Veltri, Oklahoma City, Okla.; Gabor B. Fodor, Morgantown, W. Va.

[73] Assignee: Theracel Corporation, Bethesda, Md.

[21] Appl. No.: 588,073

[22] Filed: Sep. 25, 1990

Related U.S. Application Data

[63] Continuation-in-part of Ser. No. 484,224, Feb. 23, 1990, abandoned, which is a continuation-in-part of Ser. No. 226,185, Jul. 28, 1988, abandoned, which is a continuation-in-part of Ser. No. 82,052, Aug. 5, 1987, abandoned, which is a continuation-in-part of Ser. No. 857,291, Apr. 29, 1986, abandoned.

[51] Int. Cl.$^5$ .................. C07D 307/88; A61K 31/34
[52] U.S. Cl. ...................... 514/470; 549/306
[58] Field of Search ................ 514/470; 549/306

[56] References Cited

U.S. PATENT DOCUMENTS 4,552,895 11/1985 Koppel et al. ............. 549/306
4,620,014 10/1986 Szent-Gyorgyi ........... 549/306

OTHER PUBLICATIONS

Fodor et al., Tetrahedron, vol. 39, No. 13, pp. 2137-2145, 1983.

*Primary Examiner*—Jane T. Fan
*Attorney, Agent, or Firm*—Wyatt, Gerber, Burke and Badie

[57] ABSTRACT

Michael addition products of ascorbic acid and selected unsaturated aldehydes and ketones are useful as immunomodulators in mammals.

22 Claims, 1 Drawing Sheet

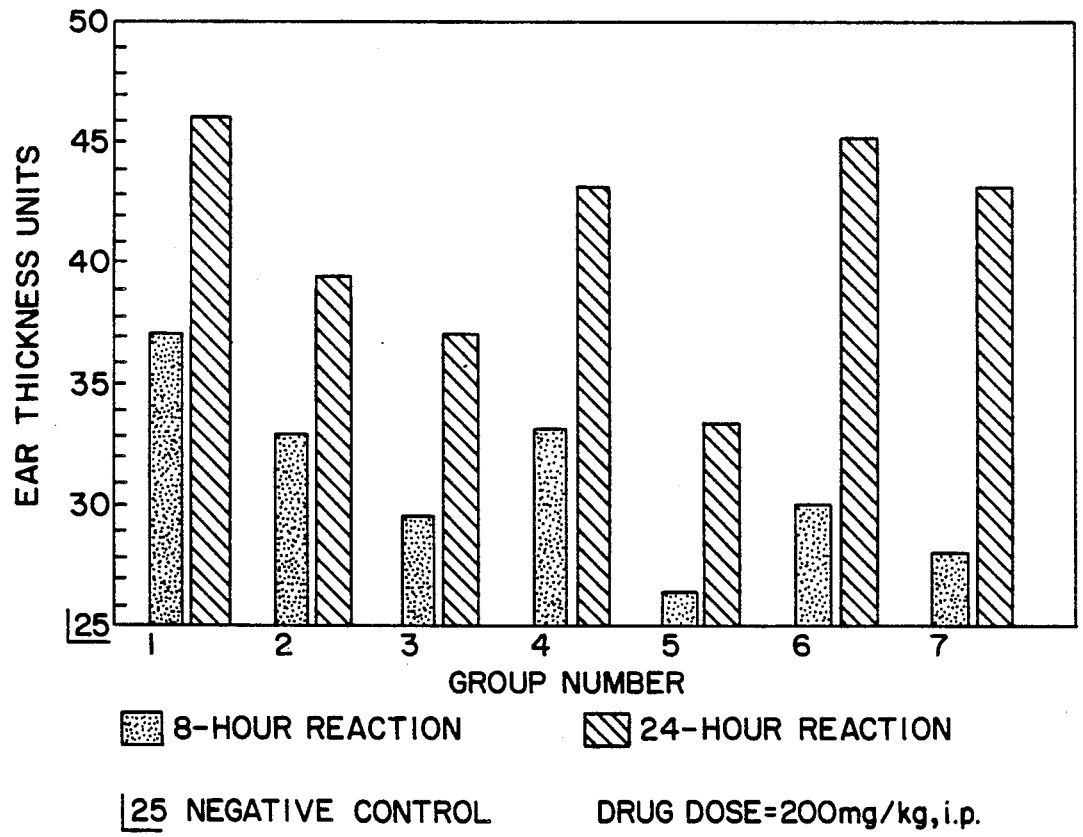

PHARMACEUTICALLY USEFUL MICHAEL ADDITION PRODUCTS OF UNSATURATED ALDEHYDES AND KETONES AND ASCORBIC ACID

RELATED APPLICATIONS

This application is a continuation in part of our co-pending and commonly owned application Ser. No. 484,224 filed Feb. 23, 1990 which is a continuation in part of application Ser. No. 226,185 filed July 28, 1988 which is, in turn, a continuation in part of application Serial No. 082,052 filed Aug. 5, 1987. This last identified application is a continuation in part of application Ser. No. 857,291 filed Apr. 29, 1986. All of these applications are now abandoned.

BACKGROUND OF THE INVENTION

This application is concerned with Michael addition products of selected unsaturated aldehydes and ketones with ascorbic acid. It includes both L-ascorbic acid and its isomer D-ascorbic acid. L-ascorbic acid is also known as vitamin C. It is concerned also with pharmaceutical compositions containing the products as the principal active ingredients, and with methods of using the products to modulate the immune response in mammals.

The compounds of this invention are useful as immunomodulating agents. They can be formulated with conventional pharmaceutical carriers for administration to animals and humans. The compounds and compositions containing them show immunomodulatory activity. As immunostimulators, they are useful for treatment of a wide variety of mammalian disorders which require stimulation of the immune system. These include, for example, stimulation of the immune system following chemotherapy or radiation therapy. The products are also useful to stimulate the proliferation of helper cells in diseases such as measles, herpes virus infections, and leprosy which are characterized by an undesirably high concentration of suppressor cells. They are also useful in the early stages of various infections to stimulate the production of interleukins, interferons, and other natural lymphokines.

Therapeutic agents useful to effect immunosuppression are extremely valuable. One such agent, cyclosporine is widely employed to prevent rejection in the case of organ transplants. The compounds of this invention have similar activity, and are also useful to inhibit the progress of autoimmune diseases such as multiple sclerosis, systemic lupus erythematosus and rheumatoid arthritis.

The immune system is one of the primary defenses against disease causing microbes and other foreign proteins in higher animals. An immune response is mediated by the action of specific antibody proteins which react to specific antigens. Antigens are substances of fairly high molecular weight, often proteins, which are foreign to an individual's body. They are most frequently located on the outer surfaces of cells. Potential antigens can be found, for example, on pollen grains, tissue grafts, some tumor cell surfaces, animal parasites, viruses, and bacteria.

In humans, many potential antigens never pass the body's first two defense lines and therefore may not provide sufficient stimulation to the immune system. These two primary defense lines consist firstly of the skin, mucous membranes, tears, and stomach acid and secondly of specialized white blood cells, granulocytes and monocytes, and macrophages which may destroy pathogens and other potential antigens by phagocytosis, that is by engulfing and destroying the foreign material. These white blood cells and macrophages are called phagocytes. When pathogens or other foreign substances do pass the body's first two defense lines, the immune response begins.

There are two principal compartments of the immune defense system, humoral and cellular, both of which react to antigens. Humoral immunity is due to circulating antibodies which are found in the gamma globulin fraction of the plasma proteins. When plasma is centrifuged at high speed or chemically precipitated with ethanol by the Cohn procedure its component proteins separate by weight or charge into sections called fractions. Antibodies are usually found in the gamma globulin fraction whose components have a sedimentation constant of about 7-10S. The IgG fraction has a molecular weight of approximately 156,000. Humoral immunity provides long term protection against bacterial and viral infections. Cellular immunity is partly due to direct lymphocyte interaction, or reactions with their products called lymphokines. This type of immunity is responsible for delayed allergic reactions, rejection of transplant of foreign tissue, and rejection of tumor cells. It is the major defense against infections due to viruses, fungi, parasites, and a few bacteria such as the tubercle bacillus and plays a key role in recovery from such infections.

Specialized white blood cells called lymphocytes are responsible for both humoral and cellular immunity. The lymphocyte precursors originate as hematopoietic tissue ontogenetically (pre-natally) in the embryo before the appearance of bone. It is first evident in the yolk sac as "blood islands", small clusters of hematopoietic cells linked with the yolk blood vessels. These islands contain the multipotential hematopoietic cells termed stem cells. As the embryo develops, hematopoietic cells invaginate into the body stock and into the mesenchymal bed in the anterior ventral portion of the abdomen contiguous with the stalk. The liver migrates into this same site of the body mesenchyme as an evagination from the gut epithelium, proliferates, and assumes the architecture of hepatic cords among hematopoietic cells. The liver thereby becomes a hematopoietic organ until close to parturition. About half way through gestation the bone cavities begin to demonstrate definite hematopoietic tissue. As mammals approach embryonic maturity hematopoiesis recedes in the liver and the bone marrow becomes the dominant hematopoietic organ.

Post-natally the lymphoid organs of the body house the immunologically competent lymphocytes which characterize the immune system. The bone marrow houses the stem cells (precursor of all myeloid and lymphoid cellular elements). Some of these stem cells migrate to one of the primary lymphoid organs of man and other mammals, the thymus. The thymus is a multi-lobed organ that lies high beside the sternum. Here, the stem cells proliferate and differentiate into mature T-lymphocytes which then enter the circulation and seed secondary lymphoid organs including the spleen, lymph nodes, tonsils, appendix, and Peyer's patches in the gut. The bone marrow also seeds the gut-associated lymphoid system, distributed along the gut, with pre-B cells. These cells then proliferate and differentiate under the influence of antigenic stimulation and migrate to the same secondary lymphoid organs described above. The T-cells and B-cells are structurally and functionally distinguishable through various biological, immunochemical and biochemical means.

Humoral immunity is mediated by the B-lymphocytes which have immunoglobulin receptors for particular antigens on their cell surfaces. They seem to be very specific and each type of B-lymphocyte reacts to only one antigen. When bacteria or viruses, for example, invade an organism, B-lymphocytes react to and combine with the antigens on the bacterial or viral surface and the lymphocyte is stimulated to divide. Its daughter cells differentiate into specialized cells called plasma cells. These cells produce and then secrete large quantities of antibodies into the general circulation. The antibodies are specific for the antigens which stimulated their production and react only with those antigens. Antibodies formed in response to antigens by the plasma cells may be functionally differentiated as cytophilic, that is they are capable of combining with cellular antigens and enhancing phagocytosis by monocytes, macrophages and polymorphonuclear granulocytes in the peripheral circulation. Such antibodies may also be cytotoxic and on combination with cellular antigens in the presence of complement may cause lysis. Other antibodies may in the presence of specific antigen-sensitized T-cells product antibody dependent cell lysis of tumor cells or virus infected cells. Antibodies produced to toxins or viruses may neutralize their toxicity or infectivity respectively by combining with the appropriate critical site for biological activity. Still other antibodies may be directed against the idiotypic determinant of an antibody molecule (the variable domain of the molecule), thereby being defined as an anti-idiotype or anti-antibodies (antibody 2) which are capable of regulating specific antibody synthesis or maintenance of antibody levels. In the latter cascade, antibody may be formed to the anti-idiotype generating a new antibody (antibody 3) with a specificity to the original antigen. The latter may be achieved without the immunized animal ever having experienced challenge with the original antigen. Such technology may be of value in modifying the course of autoimmune or malignant diseases.

Once a pathogen invades the body and the immune response begins, antibodies are made between 10-14 days later. This initial reaction is called the primary response or primary immunization. However, during that time, the pathogens have also been dividing and producing various disease symptoms. It may take days or weeks before enough antibodies are made to eliminate all the pathogens but once they disappear, the disease symptoms disappear as well. The lymphocytes, plasma cells, and antibodies remain and circulate in the blood so that if the same pathogens enter the body a second time, the B-memory lymphocytes react immediately and start antibody production. The response of these pre-sensitized lymphocytes is called the secondary response. The secondary response results in the production of higher levels of antibody than were currently circulating in the plasma. So many antibodies are produced so rapidly that the microbes are unable to establish themselves, divide, and cause disease under the latter circumstances.

Humoral immunity produced by the IgE isotype of immunoglobulin has as one of its efferent reactions immediate hypersensitivity due to the fact that a previously exposed organism can respond within minutes to an antigen, as in the case of hay fever. Another example of immediate hypersensitivity would be anaphylactic shock, an extreme allergic reaction that sometimes occurs when an individual is exposed to an antigen to which he has been sensitize. Sometimes, this humoral response to the antigen can result in death.

Humoral immunity can also be both naturally and artificially induced. In the case of active natural acquired immunity, an individual's B-lymphocytes continue to circulate and activate the production of antibodies after an infection. This active natural acquired immunity lasts for many years or even a lifetime. An infant receives antibodies from the colostrum, milk secreted by the mother, the first few days after birth, which provides immunity during the first year of its life. This is known as passive natural immunity since the infant is not involved in the actual production of the antibodies. Active artificial immunity is induced by injecting dead or weakened (attenuated) microbes or synthetic antigens into an individual. These antigens can still trigger B-lymphocytes to produce antibodies against the causative pathogen. When the individual is later exposed to the virulent microbe, he is already sensitized and immediately responds with a massive secondary (memory) production of antibodies. Active artificial immunity may last many years or permanently with booster shots. There is also a form of passive artificial immunity which provides protection for about one month. This temporary immunity is brought about by injecting antibodies obtained from another person or animal into an individual. It is usually only used in crisis situations and epidemics. Because the lymphocytes are by passed, they neither make antibodies nor "remember" the antigen, which accounts for the temporary effect of this method.

In cellular immunity, as contrasted to humoral immunity, circulating antibodies are not detectable. The T-lymphocytes which mediate this type of immunity are activated when they encounter antigens on cells from another individual, as in the case of transplants, tumors, bacterial, or parasites or viruses. Like B-lymphocytes, T-lymphocytes are specific and each type reacts with only one antigen. The T-lymphocytes in the peripheral circulation are divided into subpopulations with different effector functions in the immune response. The T-helper inducer subpopulation has a specific receptor for antigen and is responsible for augmentation of the production of specific antibodies to the antigen by B-cells. The T-helper inducer is identified in humans by a surface marker referred to as the T-4 antigen and can be detected with monoclonal antibodies. Another key T-lymphocyte subpopulation is the T-suppressor inducer (T-8 antigen surface marker) lymphocyte which regulates the magnitude of response of certain T- and B-cells to specific antigens. There are also T-cytotoxic (killer) cells which can bind directly to target tumor or graft or virus infected cells causing their destruction. In addition when T-cells proliferate in response to antigen they product lymphokines which participate in regulation of the immune response as well as removal of the foreign antigen. T-cells are directly involved in cell mediated immunity to tumor cells, virus-infected cells and other cellular antigens and clearly help in recovery from such disease processes. Also, the T-cells are responsible for allograft rejection, delayed, cutaneous hypersensitivity (DCH), chemical sensitization to poison ivy, oak, sumac as well as certain metals. This DCH reaction is called such because it takes 24–48 hours to develop subsequent to exposure to the antigen. Cellular immunity to new antigens usually occurs a few days before the primary (IgM) antibody response occurs in mammals and there are memory T-cell which are responsible for long term immunity. Another T-cells lymphocyte subpopulation is the natural killer (NK) T-cells (large granular lymphocytes) and these cells are called into action without prior antigenic provocation. These NK cells are active against tumors or virus infected cells and they can be stimulated to higher levels of activity (proliferation) by interferon. These cells are said to provide a key role in "immune surveillance" against cancer. T-cells as mentioned above, secrete lymphokines, a diverse and potent array of biologically active molecules with a variety of effects. Some select examples of these T-cell lymphokines include the interleukin 2 (T-cell growth factor), B-cell growth factor, interferon (gamma), and macrophages produced lymphokines (IL-1). These lymphokines serve at least two roles in the immune response, one is the regulation of immunity and the other is actual direct cytotoxicity (destruction) of tumor cells or virus-infected cells.

Immunomodulating agents activate or inhibit the process of lymphocyte proliferation. Normal lymphocyte proliferation is due to various interactions between antigens, macrophages, T- and B-lymphocytes. Additionally, certain B-lymphocytes can be activated by T-lymphocytes while others are independent of the T-lymphocytes and are activated only by antigens directly. Activated T-lymphocytes can cause macrophages to produce a molecule known as interleukin 2 (IL-2) which in turn activates T-cells, which then stimulate other T- and B-lymphocytes. Activated macrophages can produce a molecule known as interleukin 1 (IL-1) which further induces T-lymphocyte activation. chemicals, called mitogens can trigger DNA synthesis and mitosis, which are signs of activity in T- and B-lymphocytes. Some mitogens affect only one type of lymphocyte while others affect many types. Immunomodulating agents of various kinds and in varying amounts affect the complex interactions between the components of the immune system. The compounds and compositions of this invention act as immune stimulators and affect both T- and B-lymphocytes.

The immune system has been linked to some aspects of aging and may be important in protecting against cancer. The system is necessary for the recognition of changing or aging cells, such as worn out red blood cells, and their subsequent destruction, and for this reason is vital to normal body functions. One theory in the case of cancer is that the transformation of cells to the malignant state may occur fairly frequently but these changed cells are recognized as "not self" and destroyed. Some carcinogens may work by depressing the immune response rather than by transforming cells themselves to a malignant state. This would mean that the body would no longer destroy the spontaneously transformed cells and a cancerous growth could escape, resulting in a tumor. Immunostimulation could be useful in treating such cancers.

Also, certain tumors which develop in man produce as a result of their growth an immunodepressed state in the host (i.e. leukemias, lymphomas, respiratory cancers, and HTLV inducted tumors).

Some of the methods of treating cancer, surgery, cytotoxic chemotherapy, and radiation for example, can result in a suppression or drastic variation of the normal functions of the immune system. Immunostimulatory drugs, such as the compounds and compositions of this invention can be very effective is combating and/or preventing various infections which can result due to the depressed immune system.

OBJECTS OF THE INVENTION

An object of the invention is to provide compounds of low toxicity having immunomodulatory activity.

Another object of the invention is to provide methods for producing such compounds, some of which are novel.

Another object of the invention is to provide novel compositions effective in the treatment of immune disorders.

Other objects, advantages and novel features of the invention will become apparent from the following detailed description.

DESCRIPTION OF THE INVENTION

It has now been discovered that the acid catalyzed Michael reaction products of ascorbic acid and certain selected ketones are useful as immunomodulators. More specifically, the useful reaction products of the invention are those obtained by reactions of ascorbic acid with α,β-unsaturated-alicyclic ketones containing from 4 to 7 carbon atoms, or with vinyl aliphatic ketones in which the saturated moiety of the aliphatic ketone contains from 1 to 5 carbon atoms. The alicyclic and aliphatic moiety may be substituted with any of a variety of reaction inert substituents particularly electrophilic substituents such as lower alkyl, especially alkyl containing up to four carbon atoms or similar haloalkyl groups, especially lower alkyl groups containing chlorine or fluorine such as trifluoromethyl.

Preferred compounds of the invention may be represented by the formulas:

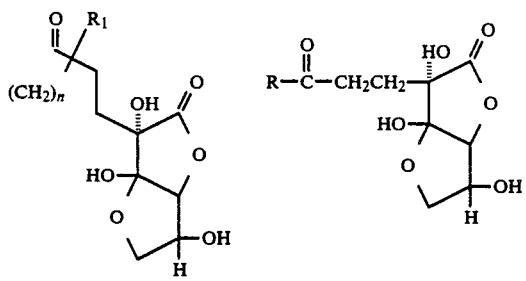

wherein: R represents a lower alkyl group, suitably one, containing from 1 to 5 carbon atoms, $R_1$ is hydrogen, lower alkyl or lower haloalkyl with the proviso that $R_1$ cannot be at the 3-position and n is 2, 3 or 4. In the alicyclic compounds, the $R_1$-cannot be on a carbon atom which is β to the carbonyl group.

Typical compounds within the scope of this invention include the reaction products of methyl vinyl ketone, 2-cyclopentenone, 2-cyclohexenone and D or L-ascorbic acid. The structures of these compounds may be represented by the following formulas:

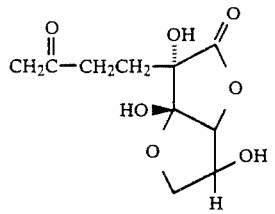

KBBL
2-(3'ketobutyl)-3-keto-L-
gulonolactone-[3,6]-cyclohemiketal

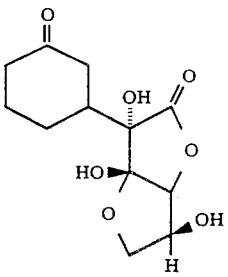

KCBL
2-(1'keto-3'S/R-cyclohexyl)-
3-keto-L-gulonolactone-[3,6]-
cyclohemiketal

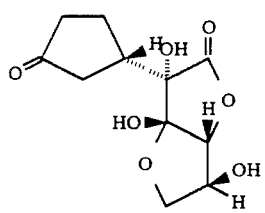

L-KCPBL-A
2-(1'-keto-3'S-cyclopentyl)-3-keto-
L-gulonolactone-[3,6]-cyclohemi-
ketal

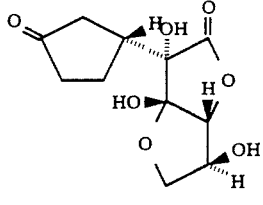

L-KCPBL-B
2-(1'-keto-3'R-cyclopentyl)-3-
keto-L-gulonolactone-[3,6]-
cyclohemiketal

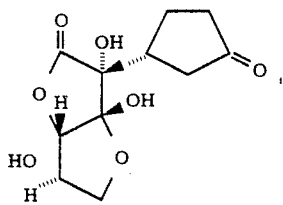

D-KCPBL-A
2-(1'-keto-3'R-cyclopentyl)-3-keto
D-gulonolactone-[3,6]-cyclohemi-
ketal

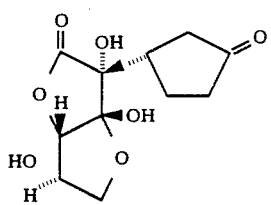

D-KCPBL-B
2-(1'-keto-3'S-cyclopentyl)-3-
keto-D-gulonolactone-[3,6]-
cyclohemiketal The chemical names for these compounds are shown beneath their respective formulas.

Presently preferred compounds within the scope of the invention are those in which the alicyclic ring of the ketone is unsubstituted and contains 5 or 6 carbon atoms and those in which the aliphatic moiety contains 1 or 2 carbon atoms and is unsubstituted. These are preferred because of their activity and because the starting compounds are readily and economically available. 3-Methyl-2-cyclohexenone does not react under the same conditions with ascorbic acid. 2-Cycloheptenone reactions, but very sluggishly.

Those skilled in the art will recognize that several stereoisomers of the compounds of this invention may exist. The most obvious are those based on L- and D-ascorbic acid as shown in the above formulas. However, as is known, further isomers of each of these isomers also exist, i.e. the 5-isoascorbic acids. D-iso KBBL, for example is prepared from D 5-isoascorbic acid. So far as is known all isomers of the compounds of the invention have some activity, although certain of them are undoubtedly more active than others as is usually the case with naturally occurring physiologically active substances. As a practical matter, it is normally most convenient to synthesize the compounds of the invention without separation of stereoisomers and to utilize the stereoisomeric mixtures so produced. As will be seen in the examples, in at least some instances, it is not exceedingly difficult to separate some stereoisomers within the scope of the invention. Applicants herein have followed the conventional practice in the specification and claims, i.e. unless specifically described or claimed the formulas employed include the stereoisomeric modifications.

The reaction is carried out in an aqueous medium at ambient temperatures in the presence of a catalytic amount of a strong inorganic or organic acid, suitably a mineral acid such as sulfuric or a halogen acid, preferably hydrochloric acid. Preferably the reaction is conducted in an inert atmosphere such as nitrogen or helium.

The preferred reaction medium is water, although other solvents may be added, especially water miscible solvents such as lower alkanols, typically methanol, ethanol, or cyclic ethers such as tetrahydrofuran, or ketones particularly acetone. These will assist in dissolving some of the higher molecular weight, or hydrophobic reactants.

Reaction is effected at a temperature of from about 20° C. to 45° C. for a period of from about 2 to 48 hours. The reaction period is not critical. It depends principally on the quantities of the reactants. The reaction is readily followed by conventional analytical methods to determine when it is complete, or when continued reaction is not warranted by expected increase in yield. High performance liquid chromatrography is a convenient tool.

Generally, equimolar quantities of the reactants will be employed. However, in certain instances it may be desirable to use a molar excess, e.g., up to about 10% molar excess of one of the reactants to assure as complete a reaction as possible.

As aforesaid, any of a variety of strong acids can be employed to catalyze the reaction. Typically 0.1% to 1.5% by weight of acid based on the total weight of reactants will be employed. In an aqueous medium, hydrochloric acid is preferred since it is readily removed by precipitation as a chloride salt. However, a stronger carboxylic acid such as trichloroacetic acid or trifluoroacetic acid may be used.

It is surprising go find a Michael addition reaction catalyzed by acid. Usually this type of reaction which is an addition of an active methylene compound to an activated unsaturated system is catalyzed by base.

The compounds of this invention which are based on alicyclic ketones are novel. Certain of those based on aliphatic ketones have been described. For example, the reaction product of methyl vinyl ketone and ascorbic acid was described by Fodor et al in Tetrahedron vol. 39, No. 13, pages 3137 to 2145 (1983). The reaction described in that publication is not an acid catalyzed reaction and is much less rapid than the reaction described herein. Additionally, the reaction described in the publication is far too slow to be practical for use to prepare reaction products on a large scale based on cyclic ketones.

The availability of the compounds of this invention for treatment of mammals, including humans has been established by a number of preclinical tests recognized by those skilled in the art. Their efficacy as immunomodulators both as stimulators and inhibitors has also been established by known and recognized test procedures. Descriptions of the test procedures follows.

They were generally conducted with L-KCPBL as representative of the other compounds of the invention.

PRECLINICAL TOXICOLOGY AND PHARMACOLOGY

Parenteral Toxicity—LD$_{50}$ in mice

I. OBJECTIVE

The objective of this experiment was to determine the LD$_{50}$ value for KCPBL when administered intraperitoneally to mice in a standard LD$_{50}$ test procedure.

II. METHODS

The following test protocol was employed.
A. Test Animals

The test animals were CD-1 male mice. The mean weight for these animals on the day of test product administration was 25.5 grams.
B. Test Product KCPBL (lot 101, consisting of 42% stereoisomer A and 58% stereoisomer B) was dissolved in pyrogen-free normal (0.85%) saline (NaCl).

The dosage was calculated as:

(mg/kg drug)×(kg body wt.)/0.5 ml=dose

Therefore, the dose (0.5 ml volume) per animal in each of the four treatment groups was:

(8000 mg/kg)×(0.0255 kg)/0.5 ml=204 mg BL-012 per 0.5 ml (4000 mg/kg)×(0.0255 kg)/0.5 ml=102 mg BL-012 per 0.5 ml (2000 mg/kg)×(0.0255 kg)/0.5 ml =51 mg BL-012 per 0.5 ml Vehicle Control=0.5 ml pyrogen-free normal saline Five animals constituted each treatment group.

Each mouse received 0.5 ml by intraperitoneal (i.p.) injection, using a 3.0 cc syringe fitted with a 23-gauge needle.

All mice were observed daily for signs, symptoms and survival for three days. Survival statistics were determined after third day.

Two mice were randomly selected from the control and high dose test group for sacrifice and selection of tissues for histopatholigic examination.

LD$_{50}$ was calculated by the method of Spearman & Karber: Basic Exercises in Immunochemistry, A. Nowatny (Ed); Pg 184–85, Springer-Verlag, N.J.

III. RESULTS

The following observations were made.

Among the surviving animals, there were no overt signs or symptoms observed that might be regarded as indicative of any toxic response.

Only two animals died. Both were members of the treatment group receiving the highest dose level.

TABLE 1

| BL-012 (mg/Kg) | Animal Survival Statistics | | | |
|---|---|---|---|---|
| | Day 0 | Day 1 | Day 2 | Day 3 |
| 8000 | 5 | 3 | 3 | 3 |
| 4000 | 5 | 5 | 5 | 5 |
| 2000 | 5 | 5 | 5 | 5 |
| 0 | 5 | 5 | 5 | 5 |

IV. CALCULATION OF LD$_{50}$ $$Log_{10}LD_{50} = Log_{10}[\text{highest dose}] + Log_{10}\frac{1}{2} - \frac{SR}{N}$$

D = dilution
SR = sum of dead animals
N = total animals per group $Log_{10}LD_{50} = Log_{10}(8000)$ = 0.301 (0.5 − 0.4)
= 3.903 + (0.301) (0.1)
= 3.903 + 0.0301
$Log_{10}LD_{50}$ = 3.9331
$LD_{50}$ = 8572.35 mg/kg Histopathological evaluations were performed only on tissues obtained from randomly selected control and high-dose survivors. There were no significant deviations in organ histopathology (lungs, liver, kidneys) noted between the control and 8000 mg/Kg test animals.

V. DISCUSSION AND CONCLUSIONS

This experiment was conducted as an initial screening test to provide preliminary information on the LD$_{50}$ value for a potential new antiviral compound, KCPBL. The test procedures employed standard laboratory methodology for an LD$_{50}$ test. From the data obtained in this experiment, the LD$_{50}$ value for intraperitoneal administration of KCPBL in CD-1 male mice is approximately 8572 mg/kg.

Oral Toxicity

I. OBJECTIVE

The objective of this experiment was to observe the clinical effects associated with the peroral administration of a single high dose of KCPBL to mice.

II. METHODS

The following test protocol was employed.
A. Test Animals

The test animals were CD-1 male mice. The mean weight for these animals on the day of test was 25.5 grams.

Test Product

KCPBL (consisting of 42% stereoisomer A and 58% stereoisomer B) was dissolved in pyrogen-free normal (0.85%) saline (NaCl).

The dosage was calculated as:

(mg/kg drug)×(kg body wt.)/0.5ml=dose

Therefore, the dose (0.2 ml volume) per animal for the single active treatment group and for the vehicle control group was:

(5000 mg/kg)×(0.0255 kg)=127.5 mg/0.2 ml p.o.

Vehicle Control=0.5 ml pyrogen-free normal saline

Nine animals constituted the active peroral treatment group; eight animals were used in the vehicle control group.

Each mouse received a single 0.2 ml peroral (p.o.) dose using a 1.0 cc syringe fitted with a curved gavage needle.

All mice were observed daily for signs, symptoms and survival for fourteen days. Survival statistics were determined after the fourteenth day. All surviving mice were sacrificed on the fifteenth day, selected organs removed and weighed on a AE 100 Mettler balance and then fixed in formalin for histopathologic examination.

III. RESULTS

The following observations were made.

A. Clinical Observations

No significant abnormal clinical observations were noted in either test group.

B. Survival

Only one animal died. This animal belonged to the BL-012 treatment group and died on the 12th day of the study.

C. Histopathology

All tissue samples examined, which consisted of specimens of lung, kidney, liver, spleen, and thymus from both the control and the test article groups, were found to be within normal limits.

D. Organ Weights

All organ weights were determined using an AE 100 Mettler analytical balance. These data are presented below.

TABLE 2

Individual Animal Organ Weights at Necropsy

| Group #. | Mouse # | Lung (mg) | Kidney (mg) | Liver (g) | Spleen (mg) | Thymus (mg) |
|---|---|---|---|---|---|---|
| Controls | | | | | | |
| 1 | 1 | 201.2 | 295.6 | 2.12 | 109.2 | 30.4 |
| | 2 | 207.0 | 285.2 | 1.82 | 102.0 | 24.8 |
| | 3 | 190.9 | 259.2 | 1.80 | 93.9 | 47.1 |
| | 4 | 194.3 | 307.2 | 1.42 | 138.8 | 43.3 |
| | 5 | 228.5 | 344.5 | 1.69 | 131.2 | 44.9 |
| | 6 | 215.1 | 295.4 | 1.78 | 64.6 | 35.6 |
| | 7 | 235.1 | 356.3 | 1.98 | 101.5 | 16.4 |
| | 8 | 194.1 | 430.3 | 1.80 | 102.4 | 36.6 |
| | Mean ± SD | 208.4 ± 16.6 | 321.7 ± 53.4 | 1.9 ± 1.4 | 105.4 ± 22.8 | 35.5 ± 11.4 |
| KCPBL (p.o.) | | | | | | |
| 2 | 1 | 214.6 | 274.5 | 1.93 | 147.0 | 40.4 |
| | 2 | 210.3 | 301.7 | 2.23 | 107.0 | 34.5 |
| | 3 | 202.4 | 316.5 | 1.77 | 70.5 | 20.3 |
| | 4 | 220.1 | 268.4 | 1.76 | 143.9 | 40.3 |
| | 5 | 212.4 | 290.3 | 1.77 | 112.1 | 25.2 |
| | 6 | 182.2 | 279.8 | 1.75 | 110.6 | 40.6 |
| | 7 | 210.0 | 269.7 | 1.43 | 95.4 | 7.5* |
| | 8 | 219.4 | 290.1 | 1.84 | 114.3 | 24.5 |
| | Mean ± SD | 208.8 ± 12.1 | 286.4 ± 16.7 | 1.8 ± 0.2 | 116 ± 26.7 | 29.2 ± 11.9 |

*fragment

None of the intergroup organ weight differences were found to be statistically significant at the p ≦0.05 level in a two-tail t-test, although the intergroup difference in mean kidney weights did reach a p value level of less than 0.1.

IV. DISCUSSION AND CONCLUSIONS

This study was conducted as a single-dose (5000 mg perorally) safety study in CD-1 male mice. KCPBL was dissolved in pyrogen-free saline and administered perorally to a group of nine mice. The saline vehicle alone was administered to eight control mice. One mouse in the KCPBL group died on the 12th day. No control animals died.

None of the surviving animals demonstrated any clinically significant signs attributable to compound under test. At necropsy, respective organ weights (lung, kidney, liver spleen, and thymus) did not differ significantly (p ≦0.05) between the two groups.

Immunotoxicity—Multi-dose (1000 mg/kg body weight)

The immunotoxicological potential of KCPBL was evaluated in this experiment in which the study drug was administered to CD-1 mice for fourteen days (100 or 1000 mg/kg/day), either perorally (by gavage) or intravenously (tail vein). On the fifteenth day, the mice were weighed and sacrificed. The spleen, lungs, liver, kidneys and thymus were removed from each animal, fixed in formalin and histopathologically evaluated. In addition, a differential white blood cell count was obtained for a peripheral blood sample as well as the following tests performed: spleen cell counts (performed with Coulter Counter) and lymphocyte stimulation assays using PHA, CON-A and PWM techniques.

No clinically significant weight loss was observed among the treatment groups receiving KCPBL either intravenously or perorally. All organ systems were found to be within normal limits, based upon organ weights as well as histopathological assessments, when compared to sham-injected controls. The total spleen cell counts of the control and the treated animals were not statistically significantly different. All WBC differentials were within normal limits when compared for granulocyte and mononuclear cells. In addition, the LSA response to PHA, CON-A and PWM lectins were comparable between the treated animals and the sham-injected controls.

I. METHODS

A. Mice

CD-1 mice were obtained from Charles Rivers Laboratories. The mice were quarantined for at least one week in a separate holding room prior to use in this experiment. Five mice per treatment were used. The mice were housed in a Thoren positive pressure laminar flow Maximizer caging system with each case controlled for water and air flow. The mouse rooms are maintained on a 12-hour light/dark cycle at a constant temperature of 76° F.

B. Drug

KCPBL containing approximately 50:50 ratio of the two epimers as determined by HPLC and optical rotation analysis was used in this study. An amount of drug was calculated to deliver the equivalent of 100 or 1000 mg/kg, either by the oral or intravenous route. The average weight of the mice was 29.5 grams.

IL-2 production and LSA results for PHA, CON-A, and PWM lectins were comparable between the treated and the sham-injected controls (See Table 3).

TABLE 3

Immunological Response Data Obtained in Immunotoxicological Evaluations

| Group | N | Drug Dose mg/kg | Route | Total Splenocytes × $10^7$ Cells | Lymphocyte Blastogenesis | | | | PMV:Mono ratio | IL-2 HMU/MI |
|---|---|---|---|---|---|---|---|---|---|---|
| | | | | | Con A | PHA | PWM | RPMI | | |
| 1 | 3 | 0 | Sham IV | 5.24 ± 1.95 | 13721 ± 4266 | 7811 ± 5069 | 4354 ± 3951 | 761 ± 500 | 18/82 | 10.81 ± 6.91 |
| 2 | 3 | 1000 | P.O. | 3.73 ± 0.30 | 15151 ± 627 | 8189 ± 1602 | 4896 ± 1547 | 244 ± 97 | 21/79 | 21.11 ± 13.69 |
| 3 | 3 | 1000 | IV | 3.12 ± 0.67 | 14471 ± 2913 | 4473 ± 1181 | 4402 ± 3641 | 203 ± 122 | 11/89 | 18.12 ± 10.50 |
| 4 | 2 | 100 | P.O. | 4.15 ± 0.18 | 18948 ± 3543 | 13432 ± 4075 | 6733 ± 1181 | 307 ± 52 | ND | 44.81 ± 20.8 |
| 5 | 3 | 100 | IV | 4.03 ± 0.33 | 17292 ± 3202 | 8513 ± 3950 | 7125 ± 3899 | 234 ± 116 | 10/90 | 41.15 ± 41.06 |

C. Experiment Design

The study incorporated five treatment groups into its design: group 1, sham intravenous control; group 2, 100 mg/kg/day perorally; group 3, 1000 mg/kg/day intravenously; group 4, 100 mg/kg/day perorally, and, group 5, 100 mg/kg/day intravenously. Mice were administered KCPBL daily for a total of fourteen days via the oral (0.2 ml of a 147.5 mg/ml solution or a 29.5 mg/ml solution by gavage) and intravenous route (0.2 ml of 147.5 mg/ml solution or a 29.5 mg/ml solution by tail vein) to achieve a dose of 100 or 1000 mg/kg, respectively. The test dose was prepared fresh daily and dissolved in sterile non-pyrogenic saline. On the fifteenth day the mice were weighed, sacrificed, and the spleens, lungs, livers, kidneys and thymuses removed. These organs were weighed and, except for the spleens, the formalin-fixed organs were analyzed by a veterinary pathologist. Only two randomly-selected sets of animal organs per treatment group were histopathologically evaluated since the remaining three animals were used to isolate splenic lymphocytes for use in cellular immunoassays.

D. Assays

A leukocyte differential was obtained on peripheral blood samples and spleen cell counts (performed with Coulter Counter), and an IL-2 induction assessment as well as standard lymphocyte stimulation assays using PHA, CON-A and PWM conducted.

E. Evaluation of Survival and Organ Response

All mice were observed daily for signs, symptoms and survival. Survival was assessed through the fifteenth day. All the surviving mice were sacrificed on the fifteenth day, predetermined organs removed, place in formalin, and subjected to for histopathologic examination by a veterinary pathologist.

The individual spleens of three mice from control and test groups were processed to isolate lymphocytes and the protocols for lymphocyte blastogenesis, IL-2 induction and assay were performed. The remaining two mice in each group were sacrificed and their lungs, liver, kidney, and spleen were fixed in formalin and sent to AnMed Biosafe for histopathologic examination.

III. RESULTS

A. Immunological Response

Three animals per treatment for groups 1, 2, 3, and 5, and two animals from group 4 were sacrificed for evaluation of immunological response. The total spleen cell counts of the normal control and the treated animals were not statistically significantly different. All WBC differentials were within normal limits when compared for granulocyte and mononuclear cells. In addition, the B. Survival Data Except for treatment group 4 (KCPBL 100 mg/kg perorally), all animals survived to the conclusion of the trial. In group 4, two animals were found dead on day 4 and another animal dead on day 10. Each of these deaths was believed to be attributable to difficulties encountered in administering the peroral dosage form.

No clinically significant weight loss was observed in any of the treatment groups receiving KCPBL, either intravenously or perorally. For groups 1, 2, 3, and 5 all organ systems were found to be within normal weight limits. See Table 4. Due to prior deaths and the number of animals required to perform the immunological assays, no animals from group 4 were available for organ assessment.

TABLE 4

Organ Weights Determined for Each Treatment Group

| Group | Animal | Organ (mg) | | | | |
|---|---|---|---|---|---|---|
| | | Lung | Liver | Spleen | Kidney | Tail |
| 1 | A | 240.2 | 1910 | 105.1 | 273.6 | 271.8 |
| | B | 211.7 | 1570 | 94.5 | 281.5 | 251.9 |
| 2 | A | 192.5 | 1710 | 102.6 | 271.7 | 236.2 |
| | B | 175.8 | 1780 | 103.7 | 269.8 | 229.1 |
| 3 | A | 209.1 | 1760 | 110.8 | 287.1 | 235.8 |
| | B | 177.1 | 1310 | 75.6 | 225.3 | 239.6 |
| 4 | A | N/A | N/A | N/A | N/A | N/A |
| | B | N/A | N/A | N/A | N/A | N/A |
| 5 | A | 177.9 | 1570 | 88.7 | 235.4 | 215.1 |
| | B | 192.3 | 2350 | 104.2 | 377.9 | 248.2 |

C. Histopathological Evaluations

For two animals in each of treatment groups 1, 2, 3, and 5 the following tissues were evaluated: lung, liver, kidney, spleen, thymus and tail (injection site). Histopathological evaluation disclosed that all tissues examined were considered to be within the normal range. No tissues form animals in group 4 were available for histopathological assessment.

IV. DISCUSSION AND CONCLUSIONS

Mice were administered KCPBL for fourteen consecutive days by either the oral or intravenous route and assessed for generalized toxicity as well as immunotoxicity. None of the mice showed evidence of generalized toxicity based upon weight loss, morbidity or mortality, nor any evidence of organ specific histopathology. Employing hematologic (differential) and immunologic parameters (spleen cell counts, IL-2 induction, and LSA) there was no evidence of a immunotoxic effect produced by either the 100 mg/kg or the 1000 mg/kg dose given by either route.

Pharmacology

I. OBJECTIVE

The objectives of these tests were to evaluate the pharmacokinetics of radiolabeled KCPBL when administered either perorally or intravenously to mice.

II. METHODS

A Preparation of $^3$H-KCPBL $^3$H-KCPBL was prepared from the pure drug substance KCPBL by an exchange procedure using high specific activity tritiated water. The product was purified by reverse phase high performance liquid chromatography and then freeze-dried. Analysis was carried out on $^3$H-KCPBL reconstituted in water. Specific activity was not less than 185 GBq/mmol or 5 Ci/mmol and the molecular weight of the product is 258. HPLC analysis for purity was performed using a Zorbax C8 column (25 cm×4.6) eluting with water: acetonitrile (930:70).

B. Conduct of the Mouse Experiments

In the mouse studies, 3H-KCPBL was dissolved in sterile pyrogen-free saline containing 100 mg/kg of non-radiolabeled KCPBL. The final concentration of the test article in an injection volume of 0.1 ml was 66.6 mCi. One tenth ml was administered intravenously for plasma level and tissue biodistribution studies. Peroral dosages were prepared in a manner consistent with this approach.

Tissue samples were collected and assayed as described above. The tissues evaluated for KCPBL content at four and at 24 hours after test article administration were: heart, lung, kidney, liver spleen, muscle, bond, stomach, small intestine, large intestine and brain.

III. RESULTS

Pharmacokinetic Observations in Mice

Mice were given intravenous doses of 3H-KCPBL to evaluate its biodistribution in this laboratory animal model.

After intravenous KCPBL administration there was an immediate peak serum drug level followed by a steep decline as the drug enters various tissues (See Table 5). Serum half-life for KCPBL in this experiment was between one and two hours, accompanied by a steep decline in serum drug levels over that period, followed by a relatively stable plateau evident through the final observation made (6 hours).

TABLE 5

Plasma Levels of 3H-KCPBL (mcg/ml Plasma) Achieved after Bolus Intravenous administration or after Peroral Administration

| Time (Min) | Intravenous (mcg/ml) Mean ± SD | Peroral (mcg/ml) Mean ± SD |
|---|---|---|
| 5 | 384.2 ± 128 | 25.6 ± 5 |
| 30 | 112.9 ± 14 | 76.1 ± 12 |
| 60 | 77.7 ± 17 | 38.8 ± 9 |
| 90 | 61.8 ± 3 | 58.8 ± 2 |
| 120 | 68.4 ± 8 | 40.9 ± 6 |
| 240 | 53.9 ± 8 | 79.7 ± 7 |
| 360 | 65.7 ± 11 | 59.0 ± 10 | n=3 mice per group

Drug level determinations performed for tissue samples collected at 24 hours were generally lower than those levels found at four hours post-injection. These data indicate that the drug label persists in clearly measurable amounts for at least 24 hours.

Tissue levels after bolus intravenous administration or after peroral administration were determined at four and 24 hours (See Table 6). At four hours after test product administration, the highest tissue levles of KCPBL were found in liver, gastrointestinal tract, and brain. At 24 hours, muscle and brain demonstrated the highest levels of KCPBL among the tissues evaluated. At four hours after peroral administration, the drug was principally found in the kidneys and the gastrointestinal tract while at 24 hours, the highest drug levels were found in muscle and brain.

TABLE 6

Biodistribution of KCPBL (mcg/gm) after Bolus Intravenous or after Peroral Administration to Mice

| Tissue | Intravenous 4 Hour | Intravenous 24 Hour | Peroral 4 Hour | Peroral 24 Hour |
|---|---|---|---|---|
| Heart | 10.45 ± 3.50 | 2.85 ± 1.23 | 13.64 ± 4.98 | 5.13 ± 3.37 |
| Lung | 2.60 ± 2.20 | 1.32 ± 0.46 | 2.72 ± 0.38 | 3.73 ± 3.49 |
| Kidney | 11.72 ± 1.34 | 5.35 ± 3.66 | 63.57 ± 74.0 | 10.28 ± 5.58 |
| Liver | 21.20 ± 4.78 | 25.7 ± ** | 38.03 ± 5.0 | 11.84 ± 9.58 |
| Spleen | 0.95 ± 0.36 | 0.71 ± 0.23 | 1.73 ± 0.29 | 1.71 ± 0.16 |
| Muscle | 31.97 ± 6.09 | 120.90 ± 154.0 | 40.81 ± 3.37 | 188.5 ± 124.0 |
| Bone | 12.77 ± 3.96 | 4.53 ± 0.86 | 15.02 ± 13.6 | 10.30 ± 4.72 |
| Stomach | 23.79 ± 5.96 | 10.36 ± 5.8 | 110.00 ± 118.0 | 25.72 ± 15.0 |
| Small Intestine | 58.50 ± 18.68 | 9.62 ± 6.4 | 217.50 ± 267.6 | 24.45 ± 5.3 |
| Large Intestine | 65.57 ± 14.86 | 13.67 ± 9.3 | 135.9 ± 32.5 | 21.42 ± 4.39 |
| Brain | 38.60 ± 16.90 | 34.80 ± 20.5 | 35.22 ± 1.64 | 47.30 ± 33.0 |

**data not available

The following tests were conducted on various compounds within the scope of this invention to establish their immunodmodulatory properties. It was found that at a low dosage level, e.g., about 10 to 100 mk/kg body weight they function as immunostimulators. Conversely, at higher dosage levels, e.g. about 200 to 600 mg/kg body weight they function as immunoinhibitors.

The tests used to establish immunostimulation were:
1. Lymphocyte Blastogenesis Assay
2. Jerne Hemolytic Plague Assay
3. In Vitro Production of Interleukin—2

The test used to establish immunoinhibition was:
1. The Oxazolone Test

Lymphocyte Blastogenesis Assay

This assay measures the ability of the compound under test to affect DNA synthesis and mitosis of T- and B- lymphocyte isolated from mouse spleens.

Mitogens are substances which stimulate DNA synthesis and mitosis. The mitogens used in these studies were phytohemaglutinin (PHA) which is isolated from the red kidney bean and concanavalin-A (Con-A) which is isolated form the jack bean. Con-A binds to specific receptors (glycoproteins) containing mannosyl or glycosyl moieties and stimulates all murine T-cells to synthesize DNA, divide, and release lymphokines. Con-A in a soluble form allows distinction between T- and B-cells in the mouse, because although both T- and B-cells can bind 106 molecules of Con-A per cell, only T-cells are stimulated when this lectin is presented in a soluble form. PHA stimulates only subpopulations, T-2 cells, of T-cells in the mouse. Also, Con-A stimulates the production of cytokines such as Interleukin-2 (IL-2). In humans, both T- and B-cells are probably stimulated. The activation of B-cells by PHA may be indirect and mediated by the release of soluble mediators from PHA-activated T-cells.

The lymphocyte blastogenesis test is a method to assess the ability of immunocompetent T- or B-cells to respond to a polyclonal mitogen (i.e. PHA or Con-A) or a specific antigen. It may be performed on lymphocytes obtained from mice treated with immunostimulators in vivo or the entire assay can be performed in vitro. The assay as described below uses minimal doses of polyclonal mitogens to induce blastogenesis (proliferation measure by DNA synthesis), in order to be able to assess the phenomena of amplification. Hence, the procedure is designed to test the ability of potential immunomodulators to restore normal immunlogic parameters.

The lymphocyte blastogenesis test is carried out as follows:

1. Sacrifice two mice/experimental group by cervical dislocation.
2. Immerse mice in a mild disinfectant solution (Povadyne).
3. Remove spleens and place in a sterile 6 sell plate containing 5 ml/well of RPMI-1640.
4. Make a single cell suspension by mincing spleens with a sterile toothed forcep.
5. Place cell suspension in a sterile centrifuge tube and allow large clumps to settle for 10 minutes.
6. Remove single cell suspension by pipetting supernatant into another sterile centrifuge tube.
7. Centrifuge cell suspension for 10 mins. at 1100 RPM in GLC-2B.
8. Aseptically remove supernatant and discard.
9. Resuspend cell button in 5 mls of RPMI-1640, and centrifuge. Wash cells in this manner two more times.
10. Resuspend cells in 5 mls of RPMI-1640 containing 10-15% Human AB heat-inactivated (Pel-Freeze, Rogers, AR or BioBee, Boston, Mass.).
11. Perform viable cell count using 0.25% trypan blue exclusion dye made in physiological isotonic saline. Non-viable cells stain blue.
12. Adjust viable cell concentration to $5.0 \times 10-6$ cells/ml in RPMI-1640 containing human AB sera.
13. Aliquot in sextuplicate wells of a 96 well sterile round bottom tissue culture plate with 0.1 ml/well of the various cell suspensions to be tested.
14. Add to above replicate sextuplicate cells 2.5, 5.0 or 7.5 ug/ml of Con A, and to replicate again of 10, 15 or 20 ug/ml of PHA.
15. Include in the experiment a control plate which contains the same cells group as above, but receive a 0.1 ml of media instead of mitogen.
16. Humidify plate by filling outside wells of plate with media.
17. Incubate plates of 3 C. with 5% CO-2 for 48 hours.
18. After 48 hours all wells receive 0.025 mls of a 0.4 microcurie/ml solution of C-14 methyl thymidine and incubate at 37 C, 5% CO-2 for 18 hours.
19. The cells are harvested using a brandel M-12 Cell Harvestor (Brandel, Rockfille, Md.). onto filter paper discs using phosphate buffered saline at physiological osmolarity. (285-320 mos).
20. The filter paper disks are place into Packard miniscintillation vials and allowed to dry for 18 hours.
21. Once dried, the vials are filled with 2 mls of a scintillation cocktail containing 4 liters of scintillation grade toluene, 16.0 of 2,5-diphenyloxazole (PPO) and 0.4 g of 1,4-Bis (2-(5-Phenyloxazoly) benzene (POPOP).
22. The vials are counted in a LKB 1212 Rackbeta (LKB Instruments, Gaithersburg, Md.) Liquid scintillation counter for two minutes/vial.

Tables 7 and 8 show the results of the lymphocyte blastogenesis assay on two isomer of KCBL.

Table 9 records the results of the lymphocyte blastogenesis assay with KBBL which is the Michael addition product of L-ascorbic acid and methyl vinyl ketone.

Jerne Hemolytic Plaque Assay

This assay measures the IgM or IgG isotypes of specific antibody produced by antigen used to immunize the mice. The procedure demonstrates antibody production to T-cell dependent antigens by single B-lymphocytes. The direct assay detects IgM and the indirect assay detects IgG-specific antibody.

The procedure is as follows:

Washed spleen cells are added to an agarose (FMC, Rockland, Me.) preparation containing sheep red blood cells (SRBC) and guinea pig complement. A drop of this mixture is transferred to a small petri dish; a cover slip is then placed over the drop to flatten it. The agarose prep is allowed to solidify. Then, the dishes are placed in a small humidified changer inside a CO-2 incubator overnight.

Small pinpoint cleared areas (plaques) will be observed under the cover slip. The cleared areas are caused by antibody, specific to the SRBC's being released by stimulated spleen cells and in conjunction with the complement, lyse surrounding SRBC's. These plaque forming cells (PFC's) are counted, and calculations are performed to obtain PFC's per $1 \times 10-6$ spleen cells.

| Reagents: | Sheep Red Blood Cells | Guinea Pig Complement |
|---|---|---|
| | Sea Plaque Agarose | 30 mm Petri Dishes |
| | RMPI-1640 | 22 × 22 × 1¼ cover slips |

METHODS

1. Spleens are harvested from mice according to a standard procedure and adjusted to a final concentration of 20% in RMPI-1540.
2. SRBC's are adjusted to a final concentration of 20% in RPMI-1640.
3. Reconstitute Guinea Pig Complement (GPC) (Hazelton-Dutchland Inc., Denver, Pa.) by adding several buffered duleunt directly to lyophilized GPC. Dilute 1:7 with RMPI-1540 by adding 3 ml of RPMI media to 0.5 ml complement.
4. Prepare Sea Plaque Agarose (FMC, Rockland, ME) at 0.7% to 25 ml of RPMI-1640, add 0.175 g of the agarose in a 50 ml sterile flask. Place over medium heat, use stirring bar at lowest speed to stir gently. Remove from heat prior to boiling. Place in 37 C water bath immediately.

5. Place all reagents (SRBC's, GPC and spleen cell preps) in water bath for 15 minutes to equilibrate to 37 C.
6. For each preparation to be tested, place a 12×75 mm glass test tube into rack in 37 C water bath. Add 0.7 ml of the agarose to each 12×75 tube.
7. Adjust three separate Rannin pipetman (Gilson, Middleton, Wis.) to 0.05, 0.1, 0.2 ml.
8. to the first 12×75 mm tubes containing agarose, add 0.2 ml of the first spleen cell prep. Next, add 0.05 ml of the complement. Add 0.05 ml of SRBC's. Mix very well, until SRBC's are in a uniform suspension.
9. Label the sides of both top and bottom of a petri dish to correspond to the cell group.
10. Using the 0.1 ml pipette, withdraw 0.1 ml of the agarose/cell prep and dispense into center of petri dish-top. Repeat immediately for bottom of petri dish.
11. Carefully place/drop a 22×22 mm cover slip squarely over the droplet. Do not move dishes until agarose settles and solidifies.
12. Repeat steps 6–11 for each of the remaining cell preps.
13. After agarose has solidified, transfer to small plastic humidified chamber. Place in incubator. Allow to incubate overnight at 37 C. Read results the following morning.
14. Count and record the number of hemolytic plaques per plate. Average plaque counts between the duplicate sets. Multiply the average number of plaques per group by 2.5 to obtain the number of plaque forming cells per million spleen cells.

Tables 10 and 11 record the results of the Jerne assay on the two isomers of KCBL (A and B) and on KBBL respectively.

Table 12 records the results of the same assay of KCPBL, Isomer A.

Interleukin-2 (IL-2) Assay

The bioassay uses the IL-2 growth-dependent cell line, CTLL2 as the indicator cell line to quantitate IL-2 in a biological fluid. The assay utilizes tritiated thymidine uptake by these cells as a measure of cellular proliferation. A reference standard obtained from the NCI Biological Response Modifiers Program is employed to construct a standard curve and to calculate Half Maximal Units (HMU) activity per ml. The assay was modified from one reported by Gillis et al. (J. Immunol. 120: 2927, 1978) and was recently reviewed as a clinical bioassay (Shalaby and Pallidino, In: Manual of Clinical Laboratory Immunology, 3rd Ed., p 300, American Society for Microbiology, Washington, D.C.).

METHODS

1. This entire assay is performed in a laminar flow hood to maintain complete sterility. The work area is cleaned by wiping down all surfaces with 70% ETOH.
2. Each sample is assayed in triplicate, over dilutions of ½, ¼, ⅛, and 1/16 in a 96 well flat bottom plate. A totoal of eight (8) samples may be assayed in a single 96 well plate.
3. Prepare IL-2 Media to contain 93.8% RPMI media, 5% heat inactivated Fetal Bovine Serum (FBS), 1% PenStrep antibiotic (Sigma Chemicals, St. Louis) and 0.2% 2-Mercapto-ethanol.
4. Using a clean, calibration checked Rainin P200 variable volume pipettor (Rainin Instrument Company, Incorporated Woburn, Mass.), add 0.1 ml (100 ul) of the first sample to wells A1, 2, 3 and B1, 2, 3. Moving from left to right along rows A and B, repeat the addition process, in triplicate, for the second, third, and fourth samples.
5. To wells E1, 2, 3 and F1, 2, 3, add the fifth sample as was done for the samples in step #4. Again, moving left to right along rows E and F, add the sixth, seventh, and eighth samples in triplicate.
6. Repeat the sample addition procedure for the remaining samples in additional 96 well plates.
7. Fill a sterile reaent reservoir with the prepared IL-2 media from step #2.
8. To all sample paltes, add 0.1 ml (100 ul) of IL-2 media to all wells of rows B, C, D, F, G, and H, using a clean, calibration checked, 12 channel pipettor with sterile yellow-tips.
9. All wells in rows B and F now contain 0.2 mls (200 ul) of diluted sample. Using the 12 channel pipettor, mix and transfer 0.1 ml (100 ul) of sample from each of the wells in row B to each of the Wells in row c, thus performing a two fold serial dilution. To mix sample and media, pass up and down 6 times with 12 channel pipettor before transferring.
10. Using new yellow-tips, repeat the dilution procedure for the samples of rows F, G and H.
11. Repeat the sample dilution procedure for all remaining samples in other 96 well plates. When all samples dilutions have been completed, look through the side of each plate to be sure that all wells have a uniform volume of 0.1 ml (100 ul). At this time, should any series of sample wells have a greater volume, repear the sample dilution(s) in a separate plate. Do not attempt to salvage sample dilution that may have been made in error.
12. In a separate 96 well flat bottom plate, perform a two-fold serial dilution of the designated IL-2 standard material lengthwise, rows 1–12 in replicates of four (4) wells, do so by adding 0.1 ml of standard to wells 1a, b, c and 2a, b, c.
13. Using the 12 channel pipettor with eleven (11) yellow-tips, add 0.1 ml (100 ul) of the IL-2 media to wells 2–12 of rows A, B, C, and D.
14. Using four (4) yellow-tips on the 12 channel pipettor, perform two-fold serial dilutions of the standard material from rows 2 through 11, discarding 0.1 ml (100 ul) of excess standard material from well 11. Well 12 will contain only IL-2 media, serving as a zero control well.
15. Thoroughly mix the CTLL-2 cells in their passage flask with a ten (10) ml pipette. Transfer the contents of the flask to 50 or 250 cc conical bottom centrifuge tube. Cells are centrifuged for ten (10) minutes at 1000 rpm in the Sorvall RT-6000 at ambient temperature. Aseptically, discard the supernatant, gently resuspending the cell pellet in five (5) mls of IL-2 media.
16. Calculate cell concentration and viability by taking a cell count on a hemacytometer. Adjust cells to a concentration of then thousand cells per ml ($1 \times 10$) in IL-2 media.
17. Using a new, sterile reagent reservoir and the 12 channel pipettor with twelve (12) yellow-tips, add 0.1 ml (100 ul) of the CTLL-2 cells, row by row, to all sample and standard containing wells.

18. Incubate all sample and standard plates in a 37C incubator, 5% carbon dioxide (CO2) humid atmosphere for eighteen (18) hours.
19. Using the 12 channel pipettor with twelve (12) yellow-tips, add 0.025 (25 ul) of pre-diluted (prepared) tritiated thymidine (3H-Tdr) to all sample and standard wells.
20. After radioisotope pulisng, incubate all paltes for six (6) hours. The cellular contents of all wells are harvested onto filter-fiber strips (as per cellharvesting SOP). After drying, transferred to scintillation vials, 2.5 mls of scintillation cocktail fluid is added to each vial, and counted on the LKB Rack-Beta scintillation counter (LKB Corp., Gaithersburg, Md.) according to instructions on the tritium channel.

Analysis: Values are obtained from counter as counts per minute (cpm). The average of each triplicate sample dilution count is calculated. A standard curve of known half maximal units of the IL-2 standard dilution/cpm is constructed using a PC program for generation of the least squares line of best fit. IL-2 values are thus assessed for each sample based upon the standard curve and reported.

The results of this test are shown in Table 14 which also shows the results of a number of other tests.

Oxazolone Test

In the test, mice are immunized to the chemical 4-ethoxymethylene-2-phenyl-oxazol-5-one (oxazolone) by single or multiple applications of 100 ul of a 3% (30 mg/ml) solution in acetone. Ten to 14 days later, the immunized mice were challenged by the application of a 1% solution of oxazolone in acetone to the outer surface of the ear 60 minutes after administration of compounds of this invention. Control animals were challendged with acetone only.

The immune response of the animals to oxazolone was measured as swelling of the ear as measured by increase in ear thickness measured with a caliper.

Down regulation of the immune response was measured as a decrease in swelling of the challenged ear after treatment of the mice with test drug.

Percent inhibition of the DTH response is calculated as follows:

$$= \frac{(Oc - Vc) - (Ot - Vc)}{(Oc - Vc)} \times 100$$

Oc = Oxazolone control
Vc = Vehicle control
Ot = Oxazolone challendged, drug treated The results with six different compounds within the scope of this invention are shown in the figure. It will be noted that all show a degree of immunosuppression at the 200 mg/kg body weight compared to the controls.

TABLE 7

| EFFECT OF KCBL-A ON THE LYMPHOCYTE BLASTOGENESIS ASSAY | | | | | |
|---|---|---|---|---|---|
| DRUG DOSE mg/kg | RPMI CONTROL | PHA 14 ug/ml | % INCREASE | CON-A 6 ug/ml | % INCREASE |
| 0 | 103.0 +/−14.0 | 1727.0 +/−77.0 | — | 3612.0 +/−276.0 | — |
| 12.5 | 94.0 +/−18.0 | 1450.0 +/−50.0 | — | 3412.0 +/−251.0 | — |
| 25.0 | 77.0 +/−12.0 | 2178.0* +/−139.0 | 26.1 | 5657.0* +/−408.0 | 56.6 |
| 50.0 | 50.0 +/−8.0 | 2369.0* +/−132.0 | 37.1 | 5059.0* +/−408.0 | 40.0 |
| 100.0 | 76.0 +/−9.0 | 2384.0* +/−170.0 | 38.0 | 4104.0 +/−1287.0 | 13.6 |

*Significant increase over the controls (p 0.05); +/− refers to standard deviation.

TABLE 8

| uz,3/41 EFFECT OF KCBL-B ON THE LYMPHOCYTE BLASTOGENESIS ASSAY | | | | | |
|---|---|---|---|---|---|
| DRUG DOSE mg/kg | RPMI | PHA 14.0 ug/ml | % INCREASE | CON-A 2.25 ug/ml | % INCREASE |
| Mean O S.D. | 43.7 | 1545.8 +/−4.2 | — +/−153-.3 | 388.2 | — +/−102.1 |
| 12.5 | 67.6 +/−7.7 | 1733.1* +/−100.0 | 12.1 | 865.6* +/−277.3 | 122.9 |
| 25 | 84.3 +/−13.1 | 3512.1* +/−779.3 | 127.3 | 1309.6* +/−230.3 | 237.4 |
| 50 | 56.2 +/−7.5 | 2540.7* +/−121.7 | 64.4 | 1130.6* +/−121.7 | 191.2 |
| 100 | 84.9 +/−9.9 | 3515.4* +/−151.9 | 127.5 | 1736.7* +/−261.1 | 347.4 |
| 200 | 52.0 +/−9.8 | 3305.8* +/−111.0 | 114.1 | 2008.0* +/−458.1 | 417.5 |

*Indicates significant increase over controls (p 0.05); +/− refers to standard deviation.

This test, also known as the delayed cutaneous hypersensitivity test (DCH) is an art recognized as a measure of inhibition of the immune system.

Table 7 and 8 show the results of the lymphocyte blastogenesis assay on two isomers of KCBL. It will be noted that both isomers gave statistically significant increases in counts per minute based upon C-14 thymidine incorporation of DNA.

TABLE 9

| DRUG mg/kg | RPMI CONTROL | PHA 10.5 ug | % INCR. | PHA 14 ug | % INCR. | CON-A 1.5 ug | % INCR. | CON-A 2.25 ug | % INCR. |
|---|---|---|---|---|---|---|---|---|---|
| 0 | 26 | 1739 | — | 2323 | — | 468 | — | 1508 | — |
|  | +5 | +113 |  | +44 |  | +194 |  | +414 |  |
| 25 | 255 | 7935* | 356 | 10994* | 373 | 3572* | 663 | 5398* | 260 |
|  | +83 | +667 |  | +152 |  | +526 |  | +449 |  |
| 50 | 92 | 4579* | 163 | 7295* | 214 | 2539* | 443 | 5802* | 285 |
|  | +24 | +776 |  | +477 |  | +436 |  | +1585 |  |
| 100 | 33 | 3540* | 103 | 4878* | 110 | 1051* | 54 | 3056 | 103 |
|  | 6 | +768 |  | +428 |  | +344 |  | +937 |  |
| 200 | 55 | 47-7* | 171 | 6963* | 200 | 2571* | 449 | 6891* | 357 |
|  | 60 | +655 |  | +621 |  | +865 |  | +1026 |  |

*Indicates statistically significant at $p < 0.05$; +/− refers to standard deviations.

Table 9 records the results of the lymphocyte blastogenesis assay with KBBL which is the Michael addition product of L-ascorbic acid and methyl vinyl ketone. As will be observed the compound is stimulatory at all the doses of PHA and Con-A tested as well as at all doses of the drug used to reat the mice prior to the assay.

TABLE 10

EFFECT OF KCBL A AND B ON THE JERNE ASSAY

| | KCBL-A | | KCBL-B | |
|---|---|---|---|---|
| DRUG TREATMENT | PFC/1 MILLION CELLS | % INCREASE | PFC/1 MILLION CELLS | % INCREASE |
| VEHICLE CONTROL | — | — | 3.75 | — |
| SREC CONTROL | 56.25 | — | 47.50 | — |
| 200 mg/kg | 177.50 | 215 | 128.75 | 171 |
| 100 mg/kg | 235.00 | 318 | 157.5 | 232 |
| 50 mg/kg | 165.00 | 193 | 151.25 | 218 |
| 25 mg/kg | 115.00 | 104 | 66.25 | 39 |
| 12.5 mg/ml | 112.00 | 100 | — | — |

TABLE 11

EFFECT OF KBBL ON THE JERNE ASSAY

| TREATMENT GROUP | PFC/1 MILLION CELLS | % INCREASE |
|---|---|---|
| VEHICLE CONTROL | 0.5 | — |
| SRBC CONTROL | 23.5 | — |
| KBBL 200 mg/kg | 48.5 | 106.4 |
| KBBL 100 mg/kg | 48.0 | 104.3 |
| KBBL 50 mg/kg | 36.0 | 70.2 |

Tables 10 and 11 record the results of the Jerne assay on the two isomers of KCBL (A and B) and on KBBL respectively. All three drugs manifested a dose dependent increase compared to the control.

TABLE 12

EFFECT OF L-KCPBL-A ON THE JERNE ASSAY

| TREATMENT GROUP | PFC/1 MILLION CELLS | % INCREASE |
|---|---|---|
| VEHICLE CONTROL | 7.5 | — |
| SRBC CONTROL | 48.75 | — |
| KCPBL 200 mg/kg | 147.5 | 202% |
| KCPBL 100 mg/kg | 107.5 | 120% |
| KCPBL 50 mg/kg | 122.5 | 151% |
| KCPBL 25 mg/kg | 162.5 | 233% |

Table 12 records the results of the JERNE PLAQUE assay of L-KCPBL, Isomer A. It will be noted that this isomer stimulates T-dependent antibody production, but not in a dose response fashion.

The immunomodulatory activity of the isomeric mixture of L-KCPBL was still further evaluated in the following tests:

I. METHODS

Daily intraperitoneal injections of KCPBL were administered to normal animals and immunological responsiveness to mitogens and specific antigen evaluated.

A. Test Product—KCPBL

The test compound was weighed out immediately before use and dissolved in the injection vehicle. This solution was sterile-filtered using a 0.22 micron filter and the appropriate dose injected into mice in a 0.5 ml volume. The dose was individually calculated for each animal, based on animal weight on the first day of the experiment.

B. Test System

Inbred C57BL/6J mice were obtained from Jackson Laboratories, Bar Harbor, Me. The animals were held for one week before use in an experiment. Prior to commencement of a study, the animals were placed into groups and weighed.

C. Experimental Design

Group size ten male mice per dosage group.

Doses and schedule—Doses were selected to bracket the range generally known to be immunostimulatory in past experiments, 1, 10, and 10 mg/kg daily for four days.

Immunization—All animals except for sham controls were injected with 0.5 ml of a 2% suspension of sheep erythrocyte on day zero. This occurred two days following any pretreatment and the day before the initiation of study drug administration.

Sacrifice—Animals were sacrificed by cervical dislocation on day five. The spleens were surgically removed and the following immunological evaluations conducted.

Evaluation Parameters

1. Total splenic lymphocytes
2. Hemolytic plaque assay
3. In vitro production of interleukin-2
4. Lymphocyte blastogenesis

TABLE 13

| Panel of Assays for Immunomodulation Testing | |
|---|---|
| Parameter | Procedures |
| Immunopathology | Total Splenocyte Counts |
| Humoral Immunity | IgM Plaque-Forming Response to SRBC |
| Cellular Immunity | IL-2 Production |
| Immature lymphocytes | Con-A stimulation |
| Mature lymphocytes | PHA stimulation |
| T-dependent mitogenesis | PWM stimulation |

III. RESULTS

As an assessment of immunopathology in the above screening test panel, the cellularity of the spleen was evaluated by determination of the total number of splenocytes harvested. Humoral-mediated immunity was measured by enumerating IgM plaque-forming cells to the T-dependent antigen sheep erythrocytes. Cell-mediated immunity was evaluated as described above by determination of the ability of the splenocytes to produce the lymphokine interleukin-2 in response to stimulation by the mitogen concanavalin-A. Another measurement of cell-mediated immunity was the responsiveness of the splenic lymphocytes to the mitogens concanavalin-A (Con-A); phytohemagglutinin (PHA) and pokeweed mitogen (PWM) in the lymphocyte blastogenesis assay. In the latter test, the activation and proliferation of the lymphocytes to the mitogens represents the capability of the cells to sequentially pass from G0 to G1 and the S phse of the cell cycle. The responsiveness of the cells was measured by the uptake of radiolabeled 14C-thymidine.

The immnomodulatory effects of KCPBL seen in the screening assays are presented in Table 14. The table presents the results obtained when normal C57BL/6 mice received antigen followed by treatment with KCPBL. A significant increase in PFC was seen in the animal groups that were treated with KCPBL at 100 and 10 mg/kg. The group treated at 1 mg/kg also demonstrated values higher than the control group but the difference was not statistically significant. The immunostimulatory effect of the drug was also evident in the IL-2 assay where splenocytes removed from drug-treated animals produced significantly more IL-2 than controls in culture. In teh blastogenesis assay, significant increases in the responsiveness of drug treated splenocytes to PWM correlates with the changes seen in the other T-helper mediated functions (response to SRBC's and IL-2 production). Drug treated splenocytes were also slightly more responsive to Con-A but their reactivity to PHA was not affected.

TABLE 14

| | Effect of Treatment with KCPBL on Immune Reactivity of Normal Antigen Stimulated Mice | | | |
|---|---|---|---|---|
| | Control Group 1 | KCPBL-100 Group 2 | KCPBL-10 Group 3 | KCPBL-1 Group 4 |
| Treatment Parameters | | | | |
| N | 10 | 10 | 10 | 10 |
| SRBC | + | + | + | + |
| Drug mg/kg | 0 | 100 | 10 | 1.0 |
| Splenocytes [$\times 10^7$] | 3.14 ± 0.4 | 3.62 ± 0.4 | 3.59 ± 0.8 | 4.34 ± 0.7 |
| Anti-SRBC Plaque Forming Cells [$10^6$ Cells] | 157.8 ± 79.7 | 360.1* ± 155.4 | 280.3* ± 156.9 | 192.8 ± 59. |
| IL-2 Half Maximal Units [$10^6$ Cells] | 2.55 ± 0.8 | 4.14 ± 1.3** | 4.33 ± 1.4** | 4.48 ± 1.5** |
| Lymphocyte Blastogenesis (Counts per minute) | | | | |
| Con-A | 9321 ± 2457 | 11660* ± 967 | 10074 ± 1881 | 0491 ± 1967 |
| PHA | 5672 ± 1557 | 5849 ± 1227 | 5590 ± 864 | 5176 ± 1185 |
| PWM | 1335 ± 467 | 2086* ± 690 | 1995* ± 686 | 1977 ± 540 |
| RPMI | 57 ± 71 | 83 ± 35 | 95 ± 54 | 95 ± 66 |

*Significantly different than controls at $p < 0.05$ using Student's T-test.
**Significantly different than controls at $p < 0.05$ using Student's T-test.

IV. DISCUSSION AND CONCLUSIONS

Based on the data collected in this series of tests, KCPBL has demonstrated an immunostimulatory activity on T-helper (Th) mediated lymphocyte functions. The tests also evidence the enhancement of plaque-forming cells to sheep RBC's, interleukin-2 production and lymphocyte responsiveness to mitogens.

The biologically active compounds of this invention may be administered alone or in combination with acceptable pharmaceutical carriers, the choice of which is determined by the preferred route of administration, the solubility of the compound, the effect desired and standard pharmaceutical practice.

The oral and parenteral dosage units are prepared in accordance with standard procedures and will contian the selected active compound as the only or principal active ingredient in the composition. Any of a wide variety of known inert excipients may be exmployed to prepare compositions useful in the practice of this invention. These include, for example, dextrose, starch, talc, various types of clay, mineral oil, cottonseed or sesame oil, was compositions in which the therapeutic agent is soluble or may be suspended with the aid of known surfactants.

For buccal and sublingual adminstration the active ingredient can be formulated in tablet form with water soluble binding agents such as lactone or other palatable carbohydrates.

For rectal administration suppositories or inserts containing the active ingredient dispersed in such reagents as cocoa butter, petrolatum or other natural lubricants or in a synthetic emmollient such as polyethylene glucol 1000 or polyethylene glycol 4000 may be used.

It is convenient to administer the active agents of this invention from sustained release dosage forms. This avoids the necessity of constant clock watching or interruption of normal daily activities. A number of compositions suitable for such preparations are known and can be usefully employed.

For oral administration, the selected therapeutic agent may be in a time disintegrating tablet or pellet coated with varous thickness of known materials such as carnauba wax, cellulose esters and ethers, fats, keratin, gluten or various natural or synthetic esters. Tablets in which the selected agent is contained in a slowly dissolving core such as a core of stearic acid or castor oils are useful. Mixed release granule tablets comprising mixtures of the drug itself and the drug in separate particles coated with materials which dissolved at different rates such as dehydrogenated castor oil or fatty acids can also be employed. Alternatively the active material can be bound to an ion exchange resin such as a fulfuric acid type cation exchange resin.

A number of transdermal formulations are possible for use in the practice of this invention. They are discrete dosage forms in construction systems which, when applied to the skin deliver the therapeutic agent through the skin at a controlled rate for systemic circulaiton. The system typically comprises an outer covering barrier, a drug reservoir which may have a rate of release controlling membrane, a contact adhesive applied to some or parts of the system at the system/skin interface and a protective layer which is removed before applying the system.

The drug reservoir is normally some type of polymer matrix such as a polyvinylpyrrolidine or a silicone polymer from which the drug is slowly released. A microporous membrane such as a polypropylene film may serve as a membrane to control the rate of release.

For intra-articular injection aqueous suspensions may be employed. In this case various suspending and wetting agents may be added to the composition to obtain a suspension not tending to settle out easily or to pack down in the bottle in which it is stored. Intramuscular and subcutaneous dosage forms may also be prepared by standard pharmaceutical practice.

The compounds may be used in association with other therapeutic agents including, for example, antibiotics or antiviral agents. It may also be useful to employ the synthetic immunostimulators in association with natural immunostimulators such as interleukin 1 and 2, or interferon or it's synthetic inducter (i.e. poly IC-LC etc.), B-cell gorwth factors, or tumor necrosis factor. They may be administered by any of the usual routes of adminstration intramuscular or intravenous.

The physician or veterinarian in attendance will determine the optimum dosage in consideration of such factors as age, weight and general health of the subject. A dose which will be effective for immunostimulation will normally be form about 1 to 50 mg/kg body weight. For suppression, an effective range is, typically, 200 to 600 mg/kg b.w. The dosage may be administered in one treatment, several treatment given over a period of time, or over an extended period of time in transdermal and other sustain release preparations.

The compositions of the invention may be made available in dosage unit forms each dosage unit, containing a therapeutically effective amount of active ingredient.

The following examples are given solely for the purpose of illustration and are not to be construed as limitations of this invention, may apparent variations of which are possible without departing from the spirit or scope thereof.

EXAMPLE 1

2-(3-Ketobutyl)-2-Hydroxy-3-Keto-4-Dihydroxyethyl Butyrolactone <3, 6> Cyclohemiketal (KBBL)

L-ascorbic acid (22.0 g, 0.125 mole) was added to 88 ml water that had been degassed for 1 hour with nitrogen. Methyl vinylketone (8.75 g, 0.125 mole) was added dropwise to the resulting solution, followed by 0.3ml concentrated hydrochloric acid. The reaction mixture was allowed to stir at ambient temperature for 24 hours until HPLC analysis showed the complete consumption of methyl vinyl ketone. The HCL catalyst was removed by the addition of 2.0 g silver carbonate. The filtrate, after centrifugation, was frozen and freeze-dried to give 28.80 g (94%) of crude product. The solid was dissolved in 550 ml boiling—ethyl acetate, which upon cooling gave 13,74 g of white crystalline solid. Concentration of the filtrate gave 3.35 g of the second crop of crystalline solid. Both crops were combined and recrystallized in 450 ml hot ethyl acetate to give pure product (13.30 g, 43.3%), mp 134°-135°C., $[\gamma]^{25} = +23.1$ (C=1.02, methanol).

The corresponding ethyl vinylketone product was similarly prepared. Its melting point was 65°-67° C.

The crude second crop was recrystallized three times in hot water (147 mL, 140 mL and 100 mL) Yielding 28.75 g (11%) of pure (by HPLC), Isomer B, mp. 170°-171°, $[\gamma]22=+24.2°$ (C=2.0, methanol), $[\gamma]^{22}=+6.5$ (C=0.8, acetone).

The structures of the two isomers are:

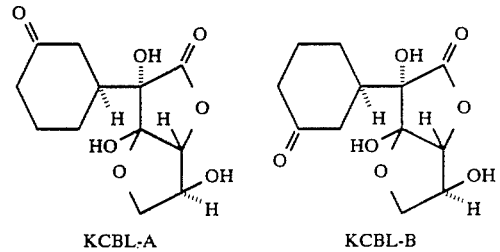

KCBL-A      KCBL-B

EXAMPLE 2

Preparation Of The Two Diasterioisomers Of L-KCPBL

2-Cyclopentenone (12.15 g, 0.148 mole) was added to a solution of L-ascorbic acid (26.05 g, 0.148 mole) in 104 ml water, followed by 1 mL of concentrated hydrochloric acid. The solution was stirred for 4 days when white solid precipitated. The crude first crop (7.02 g) was recrystallized in 5% methanol/ethyl acetate to give pure KCPBL-A (4.23 g, 11%); mp 185°-186° C.; $R_f$ (HPLC)=4.2 min. (MCH10 column—80% water/methanol—1.0 ml/min. flow rate); $[\gamma]^{20} = -49.10$ (C=2.0, methanol). Anal. Calcd. for $C_{11}H_{14}O_7$: C, 51.16; H, 5.46. Found: C, 51.01; H, 5.20.

The filtrate was concentrated to give a crude second crop (9.67 g) which is recrystallized in absolute acetone to give pure KCPBL-B (2.49 g, 7%); mp. 163°-164° C.; R (HPLC)=3.8 min. (MCH10 column—80% water/methanol—1.0 ml/min. flow rate); $[\gamma]^{23}=+92.5°$ (C=2.0, methonol). Anal Calcd. for $C_{11}H_{14}O_7$: C, 51.16; H, 5.46. Found: C, 51.21; H, 5.37.

The structure of the two isomers is:

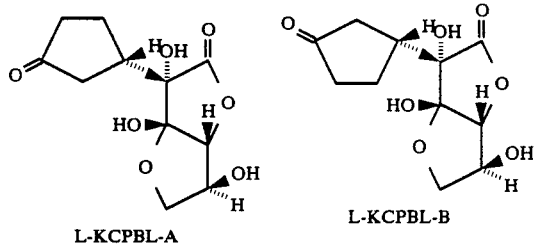

L-KCPBL-A    L-KCPBL-B

The corresponding D-isomers were similarly prepared and identified by HPLC analogs and IR spectra. There structures are:

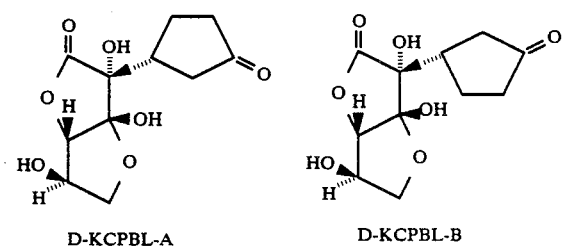

D-KCPBL-A    D-KCPBL-B

EXAMPLE 3

Tablet Formulation

| Formula: | Mg/tablet |
|---|---|
| KBBL | 200.0 |
| Citric acid | 1.00 |
| Lactose | 33.00 |
| Diacalcium phosphate | 70.00 |
| Pluronic, F-68 | 30.0 |
| Sodium Lauryl Sulfate | 15.00 |
| Polyvinylpyrrolidone | 15.00 |
| Carbowax 1500 | 5.00 |
| 3A alcohol 50 ml./1000 tablets | |
| Corn Starch | 30.00 |
| Dry: | |
| Sodium Lauryl Sulfate | 3.00 |
| Magnesium stearate | 3.00 |
| Total weight | 350.00 |

Procedure.—Mix together the KBBL, citric acid, Pluronic F-68, sodium lauryl sulfate, lactose and dicalcium phosphate. Scrren throug No. 60 mesh screen. Granulate the screened mix with an alcoholic solution containing the polyvinylpyrrolidone, Carbowax 1500 and 6000. Add additional alcohol, if necessarty, to bring powder mixt to pasty mass. Add corn starch and continue mixing until uniform damp granules are formed. Pass the damp granultation through a No. 10 screen and dry in an oven at 100° C. for 12-14 hours. Screen the dried granulation using a No. 1, screen, add sodium lauryl sulfate and magnesium stearate, mix and compress on a tablet machine to specification.

EXAMPLE 4

Capsule Formulation

| Formula: | Mg./capsule |
|---|---|
| L-KCBL Isomer A | 100.00 |
| Citric acid | 1.0 |

| -continued | |
|---|---|
| Formula: | Mg./capsule |
| Pluronic F-68 | 40.0 |
| Sodium lauryl sulfate | 20.0 |
| Lactose | 238.00 |
| Magnesium | 1.00 |

Procedure.—Mix together the KCBL, citric acid, Pluronic F-68, sodium lauryl sulfate and lactose. Pass through a No. 80 screen. Add the magnesium stearate, mix and encapsulate into the proper size 2-piece gelatin capsule.

Similar capsules are prepared with KCPBL Isomer A.

EXAMPLE 5

Parenteral Formulation

| Formula: | |
|---|---|
| L-KCBL Isomer B | mg/10 ml 200 |
| Benzyl alcohol, UF | mg/10 ml 50.0 |
| Methyl paraben, USP | mg/10 ml 18.0 |
| Propyl paraben, USP | mg/10 ml 2.0 |
| Water | ml 10 |

Procedure.—Dissolve the parabens in approximately 8.5 ml of water at 60° to 70° C. Cool the solution to 40° C. and add the benzyl alcohol. Cool the resultant solution to room temperature and add the KCBL. Place the suspension in a sterile receptacle. Fill suitably sized vials cap lossely and autoclave for one-half hourt at 110 C (15 p.s.i.g.). Each milliliter of thi formulation delivers 20 mgs. of active compound.

Similar parenteral formulations are prepared utilizing D-KCPBL Isomers A and B.

What is claimed is:

1. A compound of the formula:

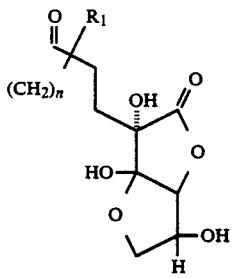

wherein n is 2, 3, or 4 and $R_1$ is hydrogen, lower alkyl or lower haloalkyl with the proviso that $R_1$ cannot be at the 3-position.

2. A compound of claim 1 in which n is 2 and $R_1$ is hydrogen.

3. The compound:

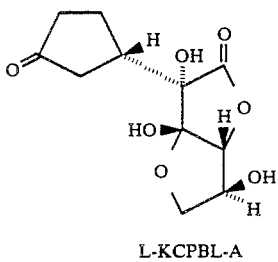

L-KCPBL-A

4. The compound:

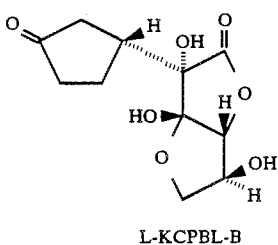

L-KCPBL-B

5. The compound:

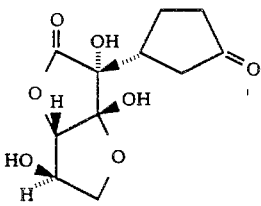

D-KCPBL-A

6. The compound:

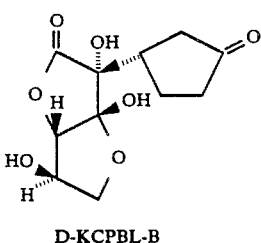

D-KCPBL-B

7. A compound of claim 1 in which in n is 3 and $R_1$ is hydrogen.

8. The compound:

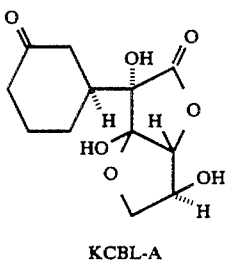

KCBL-A

9. The compound:

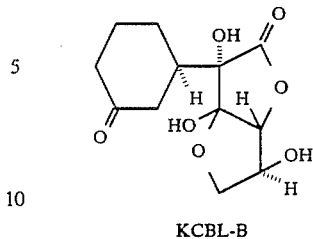

KCBL-B

10. A compound of claim 1, 2 or 7 in which the alicyclic ketone moiety is substituted on a carbon atom other than the carbon atom which is $\beta$ to the carbonyl group.

11. A pharmaceutical composition useful for immunostimulation in mammals containing a pharmaceutically acceptable carrier together with an immunostimulatory amount of a compound of the formula:

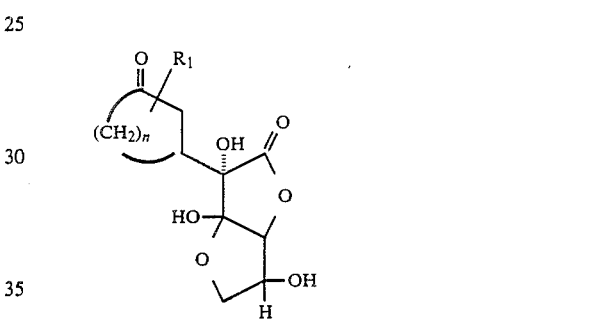

wherein n is 2, 3, or 4 and $R_1$ is hydrogen, lower alkyl or lower haloalkyl with the proviso that $R_1$ cannot be in the 3-position.

12. A composition of claim 11 which contains a compound in which n is 2 and $R_1$ is hydrogen.

13. A pharmaceutical composition useful for immunostimulation in mammals containing a pharmaceutically acceptable carrier together with an immunostimulatory amount of a compound of the formula:

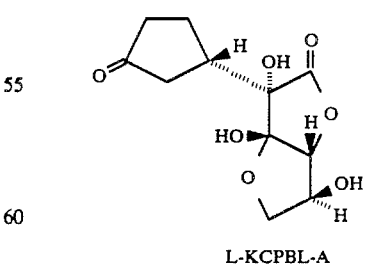

L-KCPBL-A

14. A pharmaceutical composition useful for immunostimulation in mammals containing a pharmaceutically acceptable carrier together with an immunostimulatory amount of a compound of the formula:

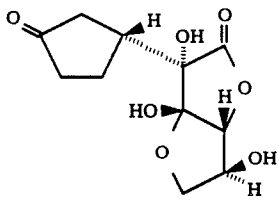

L-KCPBL-B

15. A pharmaceutical composition useful for immunostimulation in mammals containing a pharmaceutically acceptable carrier together with an immunostimulatory amount of a compound of the formula:

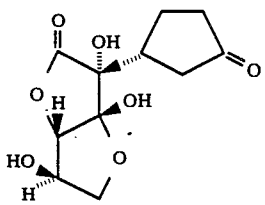

D-KCPBL-A

16. A pharmaceutical composition useful for immunostimulation in mammals containing a pharmaceutically acceptable carrier together with an immunostimulatory amount of a compound of the formula:

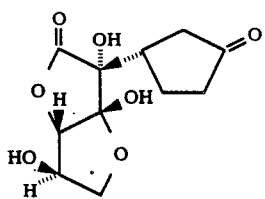

D-KCPBL-B

17. A composition of claim 9 which contains a compound in which n is 3 and $R_1$ is hydrogen.

18. A pharmaceutical composition useful for immunostimulation in mammals containing a pharmaceutically acceptable carrier together with an immunostimulation amount of a compound of the formula:

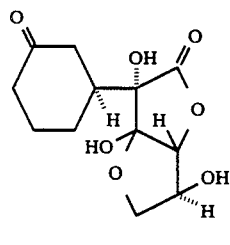

KCBL-A

19. A pharmaceutical composition useful for immunostimulation in mammals containing a pharmaceutically acceptable carrier together with an immunostimulatory amount of a compound of the formula:

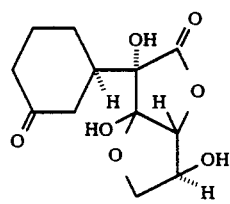

KCBL-B

20. A pharmaceutical composition in dosage unit form useful for immunostimulation in mammals containing a pharmaceutically acceptable carrier together with a compound of the formula:

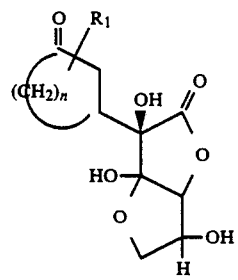

wherein n is 2, 3 or 4 and $R_1$ is hydrogen, lower alkyl or lower haloalkyl with the proviso that $R_1$ cannot be in the 3-position.

21. A method of stimulating the immune response of a mammal in need of such stimulation which comprises administering an amount which is effective to stimulate such response of a compound of the formula:

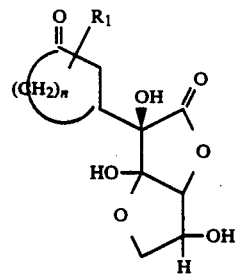

wherein n is 2, 3 or 4 and $R_1$ is hydrogen, lower alkyl or lower haloalkyl with the proviso that $R_1$ cannot be in the 3-position.

22. A method of claim 21 wherein the mammal is a human.

* * * * *